US012749161B2

(12) United States Patent
Tran et al.

(10) Patent No.: US 12,749,161 B2
(45) Date of Patent: Sep. 29, 2026

(54) METHOD AND SYSTEM FOR ECHOCARDIOGRAM SYNTHESIS WITH MYOCARDIUM MOTION MODELING USING A COMBINATION OF DIFFUSION MODEL AND NEURAL ORDINARY DIFFERENTIAL EQUATIONS

(71) Applicant: University of Engineering and Technology—Vietnam National University, Ha Noi (VN)

(72) Inventors: Quoc Long Tran, Hanoi (VN); Van Phi Nguyen, Nghe An (VN); Minh Duc Tran, Nam Dinh (VN); Huy Hieu Pham, Hanoi (VN)

(73) Assignee: University of Engineering and Technology—Vietnam National University, Ha Noi (VN)

(*) Notice: Subject to any disclaimer, the term of this patent is extended or adjusted under 35 U.S.C. 154(b) by 133 days.

(21) Appl. No.: 18/815,412

(22) Filed: Aug. 26, 2024

(65) Prior Publication Data

US 2026/0057488 A1 Feb. 26, 2026

(51) Int. Cl.
*G06T 5/60* (2024.01)
*A61B 8/08* (2006.01)
(Continued)

(52) U.S. Cl.
CPC .............. *G06T 5/60* (2024.01); *A61B 8/0883* (2013.01); *G06T 5/50* (2013.01); *G06T 5/70* (2024.01); *G06T 7/11* (2017.01); *G06T 7/20* (2013.01); *G06T 2207/10016* (2013.01); *G06T 2207/10132* (2013.01); *G06T 2207/20081* (2013.01);
(Continued)

(58) Field of Classification Search
CPC ..... G06T 5/60; G06T 7/11; G06T 5/70; G06T 7/20; G06T 2207/10016; G06T 2207/10132; G06T 2207/20081; G06T 2207/20084; G06T 2207/20212; G06T 2207/30048; A61B 8/0883
See application file for complete search history.

(56) References Cited

U.S. PATENT DOCUMENTS 12,555,367 B2 * 2/2026 Ho ........................ G06V 10/771
12,574,521 B1 * 3/2026 Luo ...................... H04N 19/132
(Continued)

FOREIGN PATENT DOCUMENTS

CN 120932161 A * 11/2025 ........... G06N 3/0442

*Primary Examiner* — John W Miller
(74) *Attorney, Agent, or Firm* — Westbridge IP LLC

(57) ABSTRACT

Disclosed are a method and a system for synthesizing echocardiogram video segments with myocardium motion modeling using a combination of diffusion model and neural ordinary differential equations. The method includes the steps of: synthesizing the video echocardiography video that conditions the segmentation map of the first frame of the cardiac cycle (end-diastole) using a video diffusion model; estimating the motion, or a diffeomorphic registration between a given frame from generated video and the first frame of the cardiac cycle using a neural ordinary differential equation (ODE) model; and obtaining an annotated echocardiogram video by propagating the segmentation map of the first frame of the cardiac cycle through the generated video using the estimated motion.

3 Claims, 4 Drawing Sheets

(51) Int. Cl.
*G06T 5/50* (2006.01)
*G06T 5/70* (2024.01)
*G06T 7/11* (2017.01)
*G06T 7/20* (2017.01)

(52) U.S. Cl.
CPC ............... *G06T 2207/20084* (2013.01); *G06T 2207/20212* (2013.01); *G06T 2207/30048* (2013.01)

(56) References Cited

U.S. PATENT DOCUMENTS

| | | | | |
|---|---|---|---|---|
| 12,586,218 | B2 * | 3/2026 | Chen | G06T 7/251 |
| 2022/0198669 | A1 * | 6/2022 | Chen | G06T 7/0016 |
| 2024/0090859 | A1 * | 3/2024 | Liu | A61B 6/487 |
| 2024/0098216 | A1 * | 3/2024 | Pottorff | H04N 19/132 |
| 2024/0303897 | A1 * | 9/2024 | Doersch | G06T 13/80 |
| 2025/0103868 | A1 * | 3/2025 | Sieniawski | G06N 3/0475 |
| 2025/0111485 | A1 * | 4/2025 | Da Costa De Azevedo | G06T 7/248 |
| 2025/0200757 | A1 * | 6/2025 | Zhu | G06T 7/20 |
| 2025/0285230 | A1 * | 9/2025 | Chickering | G06T 5/50 |
| 2026/0030766 | A1 * | 1/2026 | Yu | G06T 7/20 |

* cited by examiner

METHOD AND SYSTEM FOR ECHOCARDIOGRAM SYNTHESIS WITH MYOCARDIUM MOTION MODELING USING A COMBINATION OF DIFFUSION MODEL AND NEURAL ORDINARY DIFFERENTIAL EQUATIONS

TECHNICAL FIELD

The present application relates to a method and a system for annotated echocardiogram dataset synthesis. More particularly, the present application relates to a method and a system for synthesizing echocardiogram datasets with myocardium motion using a combination of diffusion model and neural ordinary differential equations.

BACKGROUND

In the field of medical imaging, echocardiography is a widely used imaging modality for the diagnosis and monitoring of cardiovascular diseases. Echocardiography is a non-invasive imaging technique that uses ultrasound to visualize the heart and its surrounding structures. Design of deep learning models for echocardiogram analysis requires large amounts of annotated data. However, the availability of annotated echocardiogram datasets is limited due to the high cost and time-consuming nature of manual annotation by expert cardiologists. Therefore, there is a need for a method and a system for synthesizing annotated echocardiogram datasets to facilitate the development of deep learning models for echocardiogram analysis. Prior art methods for synthesizing echocardiogram use physics-based models to simulate the motion of the myocardium or use deep learning models but do not model the motion of the myocardium. Therefore, there is a need for a method and a system for synthesizing echocardiogram datasets with myocardium motion modeling.

SUMMARY

The object of the present application is to provide a method and a system for synthesizing echocardiogram video segments with myocardium motion modeling using a combination of diffusion model and neural ordinary differential equations that overcomes the limitations of synthesis using only a single frame echocardiogram dataset from the prior art.

In order to achieve the above object, the present application provides a method for synthesizing echocardiogram datasets with motion modelling. The method comprises the steps of the follows.

A video diffusion model is used to synthesize the video echocardiography video that conditions the segmentation map of the first frame of the cardiac cycle (end-diastole).

A neural ordinary differential equation (ODE) model is used to estimate the motion, or a diffeomorphic registration between a given frame from generated video and the first frame of the cardiac cycle.

An annotated echocardiogram video is obtained by propagating the segmentation map of the first frame of the cardiac cycle through the generated video using the estimated motion.

BRIEF DESCRIPTION OF THE DRAWINGS

In order to provide a more complete understanding of the application, reference is made to the following description and accompanying drawings, in which.

DETAILED DESCRIPTION OF THE EMBODIMENTS

The present application will be described in detail with reference to the accompanying drawings.

Figure 1:
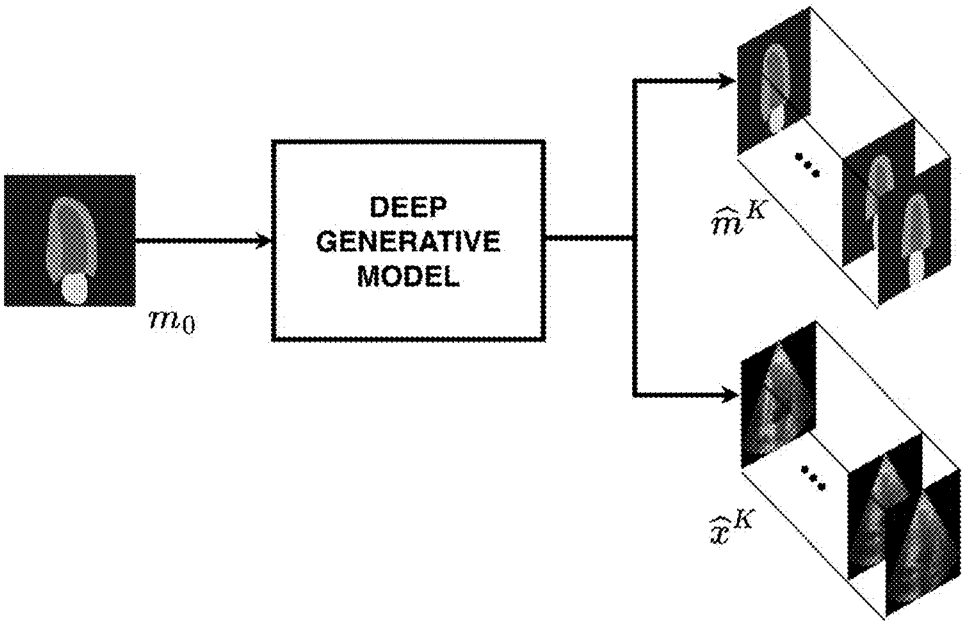
FIG. 1 is a schematic structural diagram of an overall architecture of the system, which takes a segmentation map of the first frame of cardiac cycle as input and outputs the video and segmentation maps of the remaining frames.

The first step of the method is to synthesize the echocardiogram video conditioned on the segmentation map of the first frame of the cardiac cycle (end-diastole). In the detailed description of the preferred embodiments, a method for synthesizing videos by gradually reducing Gaussian noise while leveraging semantic segmentation maps for guidance is presented. This method, as depicted in FIG. 1, entails employing Conditional Diffusion Probabilistic Models (DDPMs) and integrating semantic cues into the denoising operation.

Conditional DDPMs involve two distinct Markov processes: the forward process and the reverse process. The forward process incrementally introduces noise into the data, while the reverse process aims to eliminate it. Given a condition x, the objective of conditional DDPMs is to maximize the likelihood $p_\theta(y_0|x)$ while adhering to a prescribed distribution $q(y_0|x)$. Commencing with Gaussian noise $p(y_T)\sim N(0, \mathbf{I})$, the reverse process $p_\theta(y_{0:T}|x)$ is defined as a Markov process with learned Gaussian transitions. Formally, it is expressed as:

$$p_\theta(y_{0:T}|x) = p(y_T)\prod_{t=1}^{T} p_\theta(y_{t-1}|y_t, x) \tag{1}$$

$$p_\theta(y_{t-1}|y_t, x) = \mathcal{N}\left(y_{t-1}; \mu_\theta(y_t, x, t), \sum\nolimits_\theta (y_t, x, t)\right) \tag{2}$$

where $\mu_\theta$ and $\Sigma_\theta$ are learned functions parameterized by $\theta$.

Conversely, the forward process involves sampling data from a real data distribution $q(y_0)$ and iteratively perturbing it by adding Gaussian noise according to a specified variance schedule $\beta_1, \ldots, \beta_T$. The transition distribution is formulated as:

$$q(y_t|y_{t-1}) = \mathcal{N}\left(y_t; \sqrt{1-\beta_t}\, y_{t-1}, \beta_t I\right) \tag{3}$$

By computing $$\alpha_t = \prod_{s=1}^{t}(1-\beta_s),$$

the transition distribution of $y_t$ given $y_0$ can be derived directly as:

$$q(y_t|y_0) = \mathcal{N}(y_t; \sqrt{\alpha_t}\, y_0, (1-\alpha_t)I) \tag{4}$$

Conversely, the forward process involves sampling data from a real data distribution $q(y_0)$ and iteratively perturbing it by adding Gaussian noise according to a specified variance schedule $\beta_1, \ldots, \beta_T$. The transition distribution is formulated as:

$$q(y_t \mid y_{t-1}) = \mathcal{N}(y_t; \sqrt{1-\beta_t}\, y_{t-1}, \beta_t I) \tag{5}$$

By computing $$\alpha_t = \prod\nolimits_{s=1}^{t}(1-\beta_t),$$

the transition distribution of $y_t$ given $y_0$ can be derived directly as:

$$q(y_t \mid y_0) = \mathcal{N}(y_t; \sqrt{\alpha_t}\, y_0, (1-\alpha_t)I) \tag{6}$$

Training of conditional DDPMs involves maximizing the Evidence Lower Bound, achieved through the reparameterization trick, thereby minimizing the disparity between noise introduced in the forward process and that removed in the reverse process. The objective function at each time step t is defined as:

$$\mathcal{L}_t = \mathbb{E}_{y_0 \sim q(y_0), \epsilon \sim \mathcal{N}(0,I)} \|\epsilon - \epsilon_\theta(y_t, x, t)\|^2 \tag{7}$$

Here, tis uniformly sampled from the range [1 . . . T] and $y_0$ is sampled from the real data distribution $q(y_0)$.

In the present application context, $y_0$ represents a sequence of frames captured within a cardiac cycle ($y_0 \in \mathbb{R}^{K \times C \times H \times W}$), where K denotes the fixed number of selected frames in a video, and C, H, W denote the spatial dimensions of each frame. Additionally, each cycle is associated with an annotated semantic map of the first frame ($x \in \mathbb{R}^{C \times H \times W}$), serving as the condition for our model. This is aimed to learn a model capable of generating realistic data based on a given semantic structure.

Figure 2:
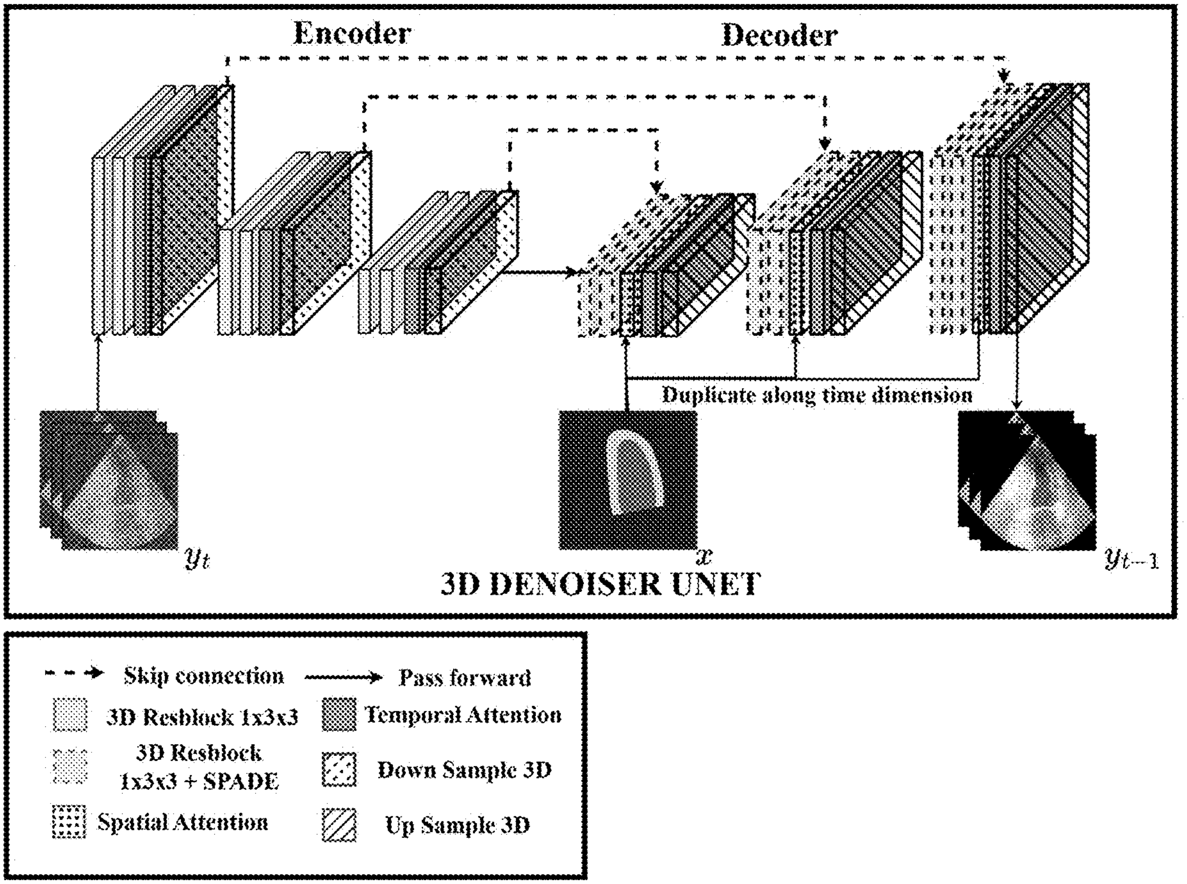
FIG. 2 is a schematic structural diagram of a spatially adaptive normalization (SPADE) block, which takes the segmentation map and the feature map as input and outputs the normalized feature map.

Furthermore, a Semantic Conditioned Diffusion Model, as depicted in FIG. 2, is provided based on the 3D-Unet architecture proposed by Ho et al. The denoising encoder processes the noisy image sequence to compute feature representations, while the decoder utilizes these features along with injected semantic information to reconstruct the original images.

To enhance the encoder's capability to handle sequences of frames, a stack of 3D Residual Convolution Blocks is employed. Each block incorporates 3D Convolution layers to compute feature representations, with temporal information t encoded using cosine embedding and then incorporated into feature outputs. Spatial and temporal relationships between frames are learned using spatial and temporal attention layers within each block.

In the decoder, each residual block is modified to effectively inject the condition information, represented by the semantic map describing the heart's structure. Inspired by recent works, Spatial Adaptive Normalization (SPADE) is adopted to add the semantic label map. Specifically, the semantic label map is injected using a SPADE layer over Group Normalization layer, enabling spatially-adaptive regulation of features.

Additionally, a classifier-free approach is employed for training the model in the present application. This involves probabilistically replacing the semantic label map x with a null label Ø during training, leading to implicit inference of the gradient of the log probability. The sampling procedure is outlined as:

$$\epsilon_\theta(y_t \mid x) = \epsilon_\theta(y_t \mid x) + s \cdot (\epsilon_\theta(y_t \mid x) - \epsilon_\theta(y_t \mid \emptyset)) \tag{8}$$

In this implementation, Ø is represented by a black image with all-zero elements.

The Semantic Conditioned Diffusion Model is trained using the Adam optimizer with a learning rate of $10^{-4}$, $\beta_1=0.9$, $\beta_2=0.999$, and a batch size of 4. The model is trained for 100 epochs, with the learning rate decayed by a factor of 0.1 every 20 epochs. The loss function is defined as the sum of the negative log-likelihood and the KL divergence between the predicted and target distributions.

The second step of the method is to estimate the motion between the generated video and the first frame of the cardiac cycle.

Deformable image registration, also known as non-rigid image registration, is a method that aligns two images by estimating a dense displacement field between them. This displacement field is typically represented as a parametric function, such as a 2D grid (Balakrishnan et al., 2018), a 3D grid (Dalca et al., 2019), or a neural network (Balakrishnan et al., 2019). Given two images $x_0$ and $x_1$ with domain Ω, the displacement field ϕ maps points from Ω in $x_0$ to corresponding points in $x_1$, and it can be expressed as $\phi(x_0)=x_1$. The estimation of the displacement field ϕ involves minimizing the following loss function:

$$L_{reg} = \mathbb{E}_{x_0, x_1 \sim p(x_0, x_1)}\left[\|\phi(x_0) - x_1\|^2\right]$$

Once the displacement field ϕ is determined, the segmentation map $m_0$ of $x_0$ can be transferred to $x_1$ by warping $m_0$ with ϕ, utilizing an appropriate interpolation technique, such as nearest neighbor interpolation:

$$m_1 = \mathcal{W}(m_0, \phi)$$

In this work, a Neural Ordinary Differential Equation (Neural ODE) is employed to estimate the registration field ϕ between the initial frame $x_0$ and the i-th frame $x_i$. With the registration field, the segmentation map $m_0$ to $m_i$ can be wrapped for each i=1, . . . , K.

The objective of this application is to synthesize temporally coherent videos comprising K frames along with their corresponding segmentation maps, conditioned solely on the segmentation map of the initial frame. Let $m_i$ denote the segmentation map of the i-th image, where i=1, . . . , K. The aim is to generate a video sequence $$x_1^K = \{x_1^1, x_2^2, \ldots, x_1^K\}$$

along with the segmentation map sequence $$m_1^K = \{m_1^1, m_1^2, \ldots, m_1^K\}.$$

Figure 3:
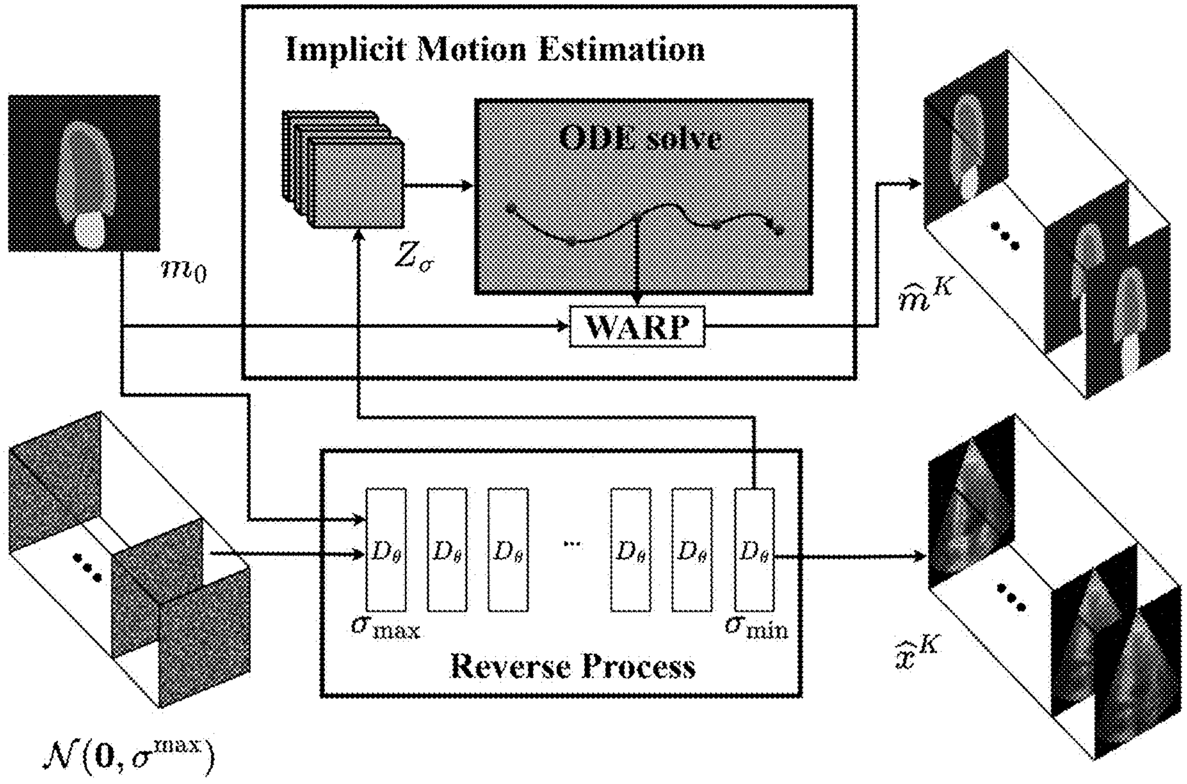
FIG. 3 is a schematic structural diagram of an overview of the sampling strategy that includes implicit motion estimation (IME) and video synthesis.
Figure 4:
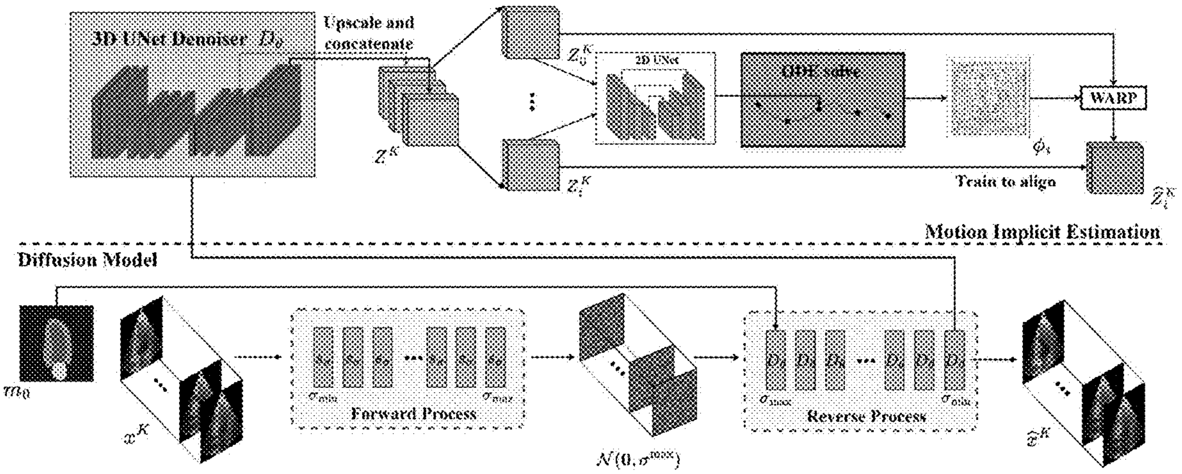
FIG. 4 is a schematic structural diagram of details of the implicit motion estimation (IME) and video synthesis.

To achieve this goal, a novel motion implicit diffusion model for medical video segmentation synthesis (MedIDM) is proposed, consisting of two separate modules: an implicit motion estimator (IME) and a 3D-UNet-based diffusion model (DM). The DM is trained to synthesize a temporally coherent video sequence conditioned on $$m_1^1,$$

while the IME is trained to estimate a continuous deformable field $\phi_i$ capable of warping $$m_1^1 \text{ to } m_1^i$$

for each i=1, . . . , K. The overall training process of MedIDM is illustrated in FIG. 4, and the inference process of MedIDM is depicted in FIG. 3. In the subsequent sections, the diffusion model is introduced, followed by the implicit motion estimator, and concluding with the training process of MedIDM.

Given the unavailability of segmentation maps for the entire sequence and the temporal inconsistency in classifying the latent space, an Implicit Motion Estimator (IME) is trained to estimate the displacement field $\phi_i$ capable of warping $m_1$ to $m_i$ for each i=1, . . . , K. To effectively train the IME, it is trained to warp the latent space of the diffusion model along the time dimension, rather than directly warping the output of the diffusion model xx. This choice is motivated by the richer semantic information present in the latent space of the diffusion model compared to its output. In practice, while training the IME alongside the Diffusion model, the IME is enabled to resist noise from the reverse sampling process. Specifically, given the latent space of the i-th frame from the diffusion model $z_l \subset \mathbb{R}^{C_z \times H_z \times W_z}$, where $C_z$ is the number of channels, and $H_z$ and $W_z$ are the height and width of the latent space, respectively, the IME is trained to minimize the following loss:

$$L_{reg} = \mathbb{E}_{i \sim \mathcal{U}(1,K), \hat{z}_0, \hat{z}_i \sim p(\hat{z}_i)}\left[\|\phi_i(\hat{z}_0) - \hat{z}_i\|^2\right]$$

where U(1, K) denotes a uniform distribution over the integers from 1 to K. The training process of MedIDM is summarized in Algorithm.

The above embodiments only illustrate the principle and effect of the present application and are not intended to limit the present application. Those skilled in the art can modify or change the above embodiment without violating the spirit and scope of the present application. Therefore, all equivalent modifications or changes made by those skilled in the art without departing from the spirit and technical ideas disclosed in the present application should still be covered by the claims of the present application.

What is claimed is:

1. A method for synthesizing temporally coherent videos comprising multiple frames and corresponding segmentation maps, comprising:

- estimating a continuous deformable field between an initial frame and subsequent frames using an implicit motion estimator;
- synthesizing a temporally coherent video sequence conditioned on a segmentation map of the initial frame using a diffusion model; and
- warping the segmentation map of the initial frame to match subsequent frames using an estimated deformable field.

2. The method of claim 1, wherein the implicit motion estimator utilizes a Neural Ordinary Differential Equation (Neural ODE) to estimate the estimated deformable field.

3. The method of claim 1, wherein the diffusion model employs a 3D-UNet-based architecture with enhanced spatial semantic information.

* * * * *